(12) United States Patent
Chen

(10) Patent No.: US 9,890,418 B1
(45) Date of Patent: Feb. 13, 2018

(54) METHOD OF DETECTING NUCLEIC ACIDS WITH ENHANCED SIGNAL USING DUAL-FUNCTIONAL CAPTURE PARTICLES

(71) Applicant: Hai Xing Chen, Toronto (CA)

(72) Inventor: Hai Xing Chen, Toronto (CA)

(73) Assignee: ACGT Corporation, Toronto (CA)

( * ) Notice: Subject to any disclaimer, the term of this patent is extended or adjusted under 35 U.S.C. 154(b) by 0 days.

(21) Appl. No.: 15/083,086

(22) Filed: Mar. 28, 2016

Related U.S. Application Data

(60) Provisional application No. 62/152,035, filed on Apr. 24, 2015.

(51) Int. Cl.
*C12Q 1/68* (2006.01)

(52) U.S. Cl.
CPC .......... *C12Q 1/682* (2013.01); *C12Q 1/6825* (2013.01); *C12Q 1/6834* (2013.01)

(58) Field of Classification Search
None
See application file for complete search history.

(56) References Cited

U.S. PATENT DOCUMENTS

2007/0015188 A1* 1/2007 Luo .................. C12Q 1/682
                                                435/6.11

* cited by examiner

*Primary Examiner* — James Martinell
(74) *Attorney, Agent, or Firm* — CUSPA Technology Law Associates; Yi Li

(57) ABSTRACT

A method of enhancing signal in detection of nucleic acid sequences utilizes dual-functional capture particles for capturing a target sequence and for binding with enhancement probes coupled to a reporter. The method includes hybridizing a target sequence with a capture sequence on dual-functional capture particles; hybridizing a pair of enhancement probes to the bounded target sequence through a linker to form a staggered chain of enhancement probes; triggering a chemical reaction between a chemical binding group on the dual-functional capture particles and a first binding moiety on the enhancement probes to bind the enhancement probes covalently to dual-functional capture particles; binding a reporter to the bounded enhancement probes through another chemical reaction between a second binding moiety on the enhancement probes and a binding functional group on the reporter; and detecting the signal from a signal generating molecule on bounded reporter, thereby amplifying signal through enhancement probes coupled to reporters.

10 Claims, 4 Drawing Sheets

T-Linker Structure

L-Linker Structure

METHOD OF DETECTING NUCLEIC ACIDS WITH ENHANCED SIGNAL USING DUAL-FUNCTIONAL CAPTURE PARTICLES

CROSS REFERENCE TO RELATED APPLICATION

This application claims the benefit under 35 USC 119 (e) of the provisional patent application Ser. No. 62/152,035, filed Apr. 24, 2015, which is hereby incorporated by reference in its entirety.

FIELD OF THE INVENTION

The present invention relates to a method of detecting nucleic acids with an enhanced signal. More specifically, the method uses dual-functional capture particles for capturing a target nucleic acid sequence and for binding with enhancement probes coupled to a reporter.

BACKGROUND OF THE INVENTION

In molecular diagnosis, the target DNA or RNA sequences in a sample are frequently at very low concentrations, which can be around or below the detection limit of available clinical diagnostic methods. This renders the analysis of these samples unreliable, or impossible. Currently, the detection limit of available methods is at the level about $10^5$ copies of the target sequence in a sample. However, a concentration of certain DNA and RNA sequences in a sample substantially below this level can be clinically significant.

The well-known PCR method was developed for solving this specific problem. In general, PCR based assays increase the concentration of a target sequence from its original concentration in the sample, and subsequently measure the target sequence after the PCR amplification. However, PCR based assays have complicated and lengthy sample preparation process, and require highly trained laboratory personals. The PCR based assays typically require up to 24 hours to obtain the analysis results.

It is desirable to be able to enhance the detectable signals of low concentration nucleic acids in a sample thereby improving detection sensitivity of an assay without relying on PCR amplification.

SUMMARY OF THE INVENTION

In one embodiment, the present invention provides a method of detecting nucleic acids with an enhanced signal. The method comprises exposing a single strand nucleic acid target sequence of interest to dual-functional capture particles, each dual-functional capture particle comprising a capture sequence complementary to a segment of the target sequence and a capturer chemical functional group, both the capture sequence and the capturer chemical functional group being immobilized on and distributed throughout a surface of the dual-functional capture particles; hybridizing the target sequence with the capture sequence on the dual-functional capture particles to form a target-capture complex; removing unbound target sequence; adding a linker comprising a target-binding segment complementary to a linker-binding segment of the target sequence and an enhancer-binding segment, and hybridizing the linker with the target sequence; removing unbound linker; adding a first enhancement probe and a second enhancement probe, the first enhancement probe comprising a first annealing segment complementary to the enhancer-binding segment of the linker, a second annealing segment, a first binding moiety at a first terminus of the first enhancement probe, and a second binding moiety at a second terminus of the first enhancement probe; the second enhancement probe comprising a first annealing segment complementary to the second annealing segment of the first enhancement probe, a second annealing segment complementary to the first annealing segment of the first enhancement probe, a first binding moiety at a first terminus of the second enhancement probe, and a second binding moiety at a second terminus of the second enhancement probe; and hybridizing the first enhancement probe with the linker, and the second enhancement probe with the first enhancement probe, wherein multiple of the first and second enhancement probes anneal with each other to form a staggered chain extending from the linker, thereby forming a capture-target-linker-enhancement probe complex; removing unbound first and second enhancement probes; triggering a chemical binding reaction between the first binding moiety at the first terminus of the first and second enhancement probes and the capturer chemical functional group on the dual-functional capture particles, thereby binding the first and second enhancement probes to the dual-functional capture particles; adding a reporter comprising a signal generating molecule and a binding functional group specific to the second binding moiety at the second terminus of the first and second enhancement probes, thereby binding the reporter to the first and second enhancement probes through the binding functional group; removing unbound reporter; detecting a signal from the signal generating molecule on bounded reporter; and determining the presence of the target sequence according to the signal.

In a further embodiment, the method comprises: exposing a single strand nucleic acid target sequence of interest to dual-functional capture particles, each dual-functional capture particle comprising a capture sequence complementary to a segment of the target sequence and a capturer chemical functional group, both the capture sequence and the capturer chemical functional group being immobilized on and distributed throughout a surface of the dual-functional capture particles; hybridizing the target sequence with the capture sequence on the dual-functional capture particles to form a target-capture complex; removing unbound target sequence; adding a linker comprising a target-binding segment complementary to a linker-binding segment of the target sequence and an enhancer-binding segment, and hybridizing the linker with the target sequence; removing unbound linker; adding a first enhancement probe and a second enhancement probe, the first enhancement probe comprising a first annealing segment complementary to the enhancer-binding segment of the linker, a second annealing segment, a first binding moiety at a first terminus of the first enhancement probe, and a second binding moiety at a second terminus of the first enhancement probe; the second enhancement probe comprising a first annealing segment complementary to the second annealing segment of the first enhancement probe, a second annealing segment complementary to the first annealing segment of the first enhancement probe, a first binding moiety at a first terminus of the second enhancement probe, and a second binding moiety at a second terminus of the second enhancement probe; and hybridizing the first enhancement probe with the linker, and the second enhancement probe with the first enhancement probe, wherein multiple of the first and second enhancement probes anneal with each other to form a staggered chain extending from the linker, thereby forming a capture-target-linker-enhancement probe complex; removing unbound first and second enhancement probes; triggering a chemical binding reaction between the first binding moiety at the first terminus of the first and second enhancement probes and the capturer chemical functional group on the dual-functional capture particles, thereby binding the first and second enhancement probes to the dual-functional capture particles; adding an intermedium coupler comprising a coupler sequence and a binding functional group specific to the second binding moiety at the second terminus of the first and second enhancement probes, and binding the intermedium coupler with the first and second enhancement probes through the binding functional group; adding a third enhancement probe and a fourth enhancement probe, the third enhancement probe comprising a first annealing segment complementary to the coupler sequence of the intermedium coupler, a second annealing segment, and a signal generating molecule at one terminus of the third enhancement probe; the fourth enhancement probe comprising a first annealing segment complementary to the second annealing segment of the third enhancement probe, a second annealing segment complementary to the first annealing segment of the third enhancement probe, and a signal generating molecule at one terminus of the fourth enhancement probe; and hybridizing the third enhancement probe with the intermedium coupler, and the fourth enhancement probe with the third enhancement probe, wherein multiple of the third and fourth enhancement probes anneal with each other to form a staggered chain extending from the intermedium coupler; removing unbound third and fourth enhancement probes; detecting a signal from the signal generating molecule on bounded third and fourth enhancement probes; and determining the presence of the target sequence according to the signal.

The advantages of the present invention will become apparent from the following description taken in conjunction with the accompanying drawings showing exemplary embodiments of the invention.

DETAILED DESCRIPTION OF THE INVENTION

Figure 1:
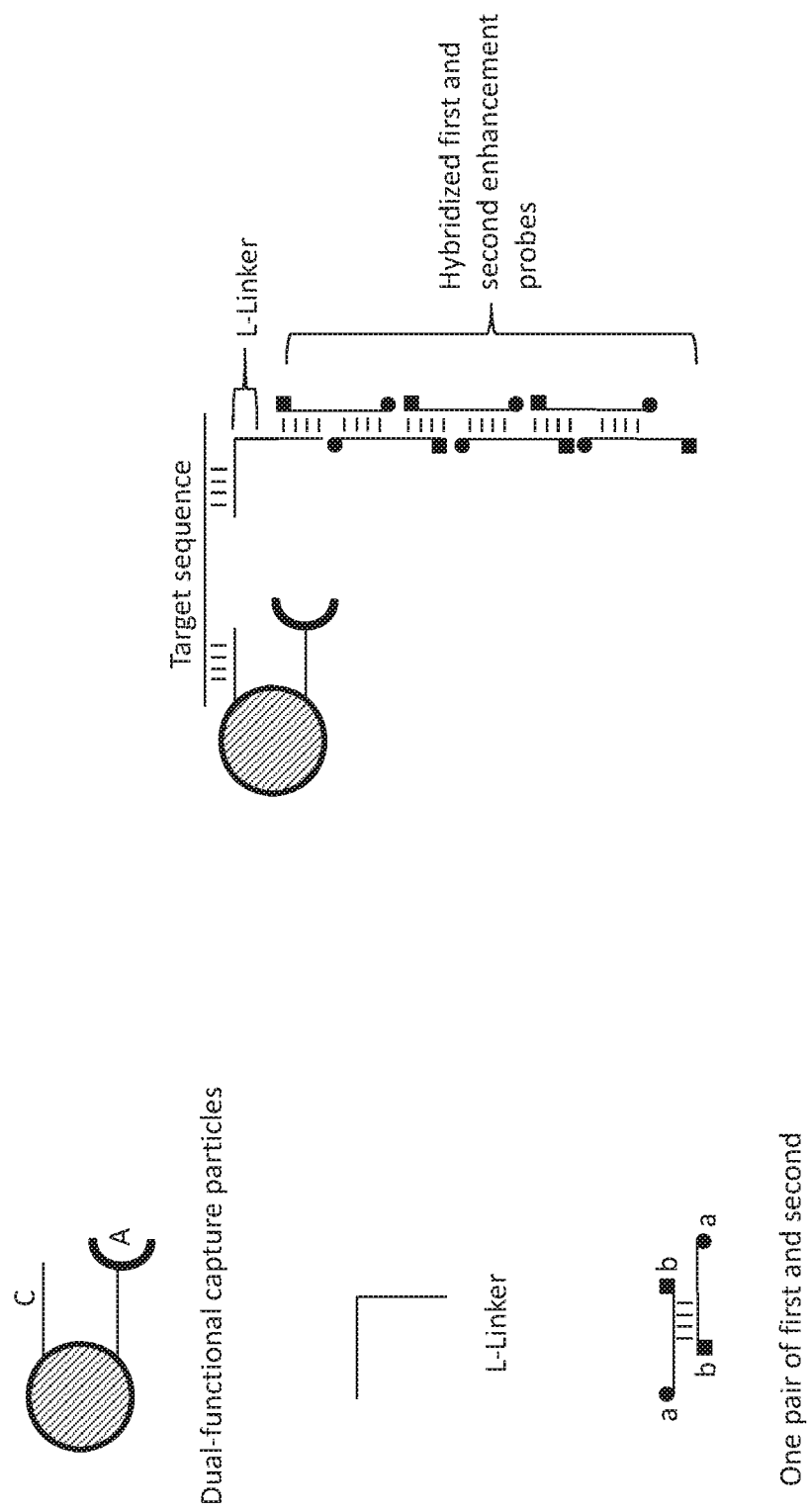
FIG. 1 illustrates schematically a capture-target-linker-enhancement probe complex formed during the process of detecting a target sequence using the method of the present invention. Individual components involved in the reactions are shown on the left.

Embodiments of the present invention generally relate to a method of detecting nucleic acids with signal enhancement. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In some embodiments, the method utilizes dual-functional capture particles for capturing a target nucleic acid sequence and for binding with enhancement probes linked to a reporter. In one embodiment, the method comprises:

(a) exposing a single strand nucleic acid target sequence of interest to dual-functional capture particles, each dual-functional capture particle comprising a capture sequence complementary to the target sequence and a capturer chemical functional group;

(b) hybridizing the target sequence with the capture sequence on the dual-functional capture particles to form a target-capture complex;

(c) removing unbound target sequence;

(d) adding a linker comprising a target-binding segment complementary to a linker-binding segment of the target sequence and an enhancer-binding segment, and hybridizing the linker with the target sequence;

(e) removing unbound linker;

(f) adding a first enhancement probe and a second enhancement probe, the first enhancement probe comprising a first annealing segment complementary to the enhancer-binding segment of the linker, a second annealing segment, a first binding moiety at a first terminus of the first enhancement probe, and a second binding moiety at a second terminus of the first enhancement probe; the second enhancement probe comprising a first annealing segment complementary to the second annealing segment of the first enhancement probe, a second annealing segment complementary to the first annealing segment of the first enhancement probe, a first binding moiety at a first terminus of the second enhancement probe, and a second binding moiety at a second terminus of the second enhancement probe; and hybridizing the first enhancement probe with the linker, and the second enhancement probe with the first enhancement probe, wherein multiple of the first and second enhancement probes anneal with each other forming a staggered chain extending from the linker, thereby forming a capture-target-linker-enhancement probe complex;

(g) removing unbound first and second enhancement probes;

(h) triggering a chemical binding reaction between the first binding moiety at the first terminus of the first and second enhancement probes and the capturer chemical functional group on the dual-functional capture particles, thereby binding the first and second enhancement probes to the dual-functional capture particles;

(i) adding a reporter that comprises a signal generating molecule and a binding functional group specific to the second binding moiety at the second terminus of the first and second enhancement probes, thereby binding the reporter to the first and second enhancement probes through the binding functional group; and (i) removing unbound reporter;

(k) detecting a signal from the signal generating molecule on bounded reporter; and (l) determining the presence of the target sequence according to the signal.

Figure 2:
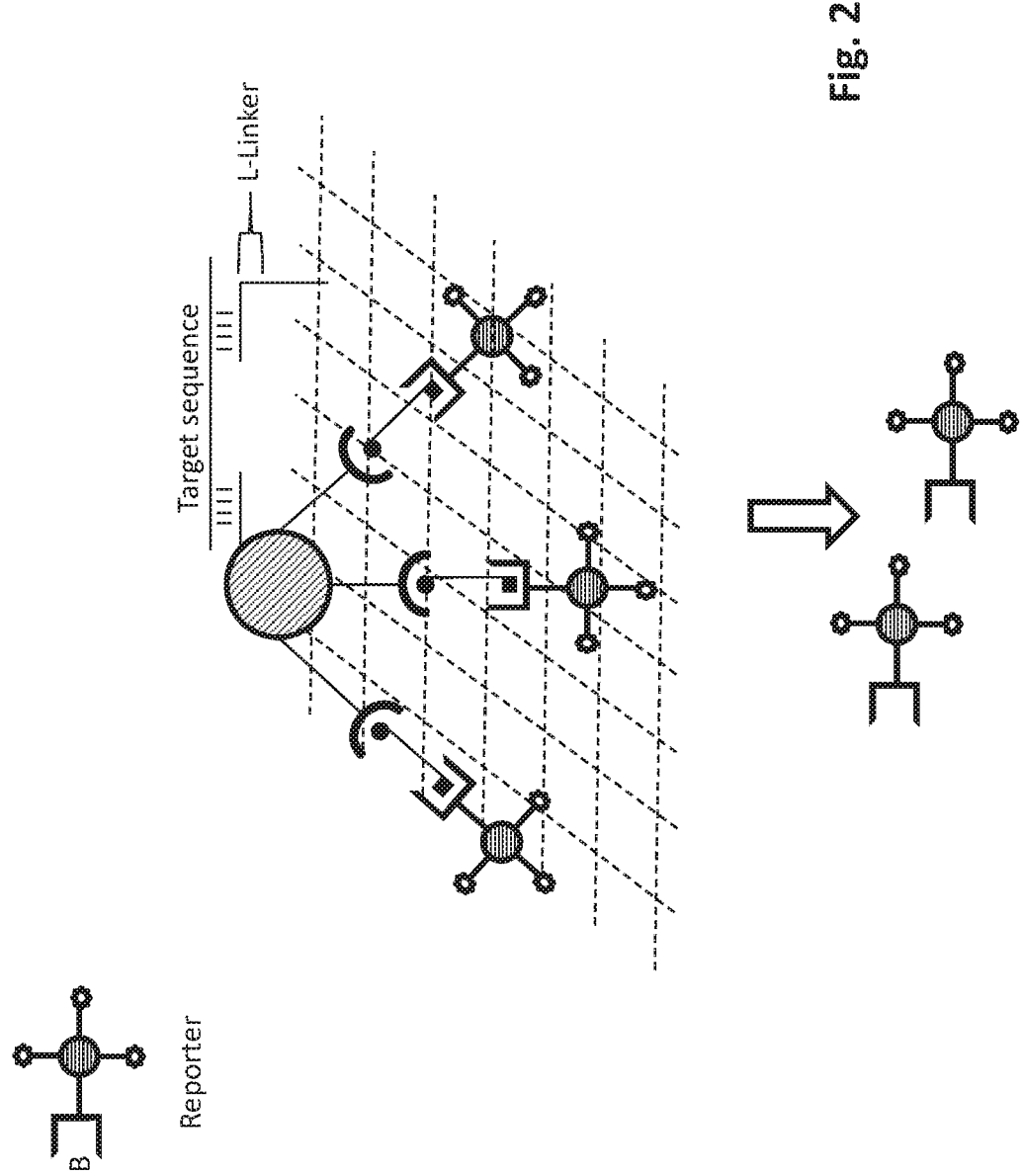
FIG. 2 illustrates schematically binding of the enhancement probes with the dual-functional capture particles and the reporter after the enhancement probes are dissociated from the capture-target-linker-enhancement probe complex shown in FIG. 1. Individual components involved in the reactions are shown on the left of FIG. 2, as well as on the left of FIG. 1.

The interactions among the target sequence, the dual-functional capture particles, the linker, the enhancement probes and reporter during the process of detection using the method of the present invention are illustrated schematically in FIGS. 1 and 2. The structural features and the interactions of the above components are described hereinafter.

The term "target sequence" used herein refers to a nucleic acid sequence to be detected, which can be a natural nucleic acid sequence in a biological sample, or a synthetic nucleic acid sequence. The target sequence has a segment that can bind to a capture nucleic acid sequence, which is herein referred to as a capture-binding segment, and another segment that can bind to a complementary sequence of the linker used for the measurement, which is herein referred to as a linker-binding segment.

In some embodiments, the dual-functional capture particles may be polystyrene particles or other polymer particles, with a diameter from about 10 to about 200 micrometer (μm). Each dual-functional capture particles comprises a single strand nucleic acid capture sequence complementary to the capture-binding segment of the target sequence of interest, and a capturer chemical functional group. Both the capture sequence (indicated by element "C" in FIG. 1) and the capturer chemical functional group (indicated by element "A" in FIG. 1) are immobilized on and distributed throughout the surface of the dual-functional capture particles. Various methods of conjugation of oligonucleotide and chemical functional groups to polymer particles can be used for making the dual-functional capture particles for the purpose of the present invention.

The capturer chemical functional group (A) of the dual-functional capture particles has a chemical binding property specific to the first binding moiety (indicated by element "a" in FIG. 1) at the first terminus of the first and second enhancement probes. Under an appropriate chemical reaction condition, the capturer chemical functional group (A) of the dual-functional capture particles binds with the first binding moiety (a) of the first and second enhancement probes, as further described hereinafter. Various known chemical functional groups can be used for the capturer chemical functional group (A), which bind specifically to the first binding moiety (a) of the enhancement probes. In some embodiments, Cu-catalyzed azide-alkyne cycloaddition reaction can be used for the binding between the capturer chemical functional group (A) of the dual-functional capture particles and the first binding moiety (a) of the first and second enhancement probes.

In one exemplary embodiment, the capturer chemical functional group (A) of the dual-functional capture particles is a propargyl functional group, and the first binding moiety (a) of the first and second enhancement probes is an azide functional group. A cycloaddition reaction to couple propargyl functional group to azide functional group is catalyzed by copper to bind the first binding moiety (a) of the enhancement probes with the capturer chemical functional group (A) of the dual-functional capture particles. Alternatively, the capturer chemical functional group (A) of the dual-functional capture particles is an azide functional group, and first binding moiety (a) of the first and second enhancement probes is a propargyl functional group. The same chemical reaction can be used for binding of the enhancement probes to the dual-functional capture particles.

Figure 3:
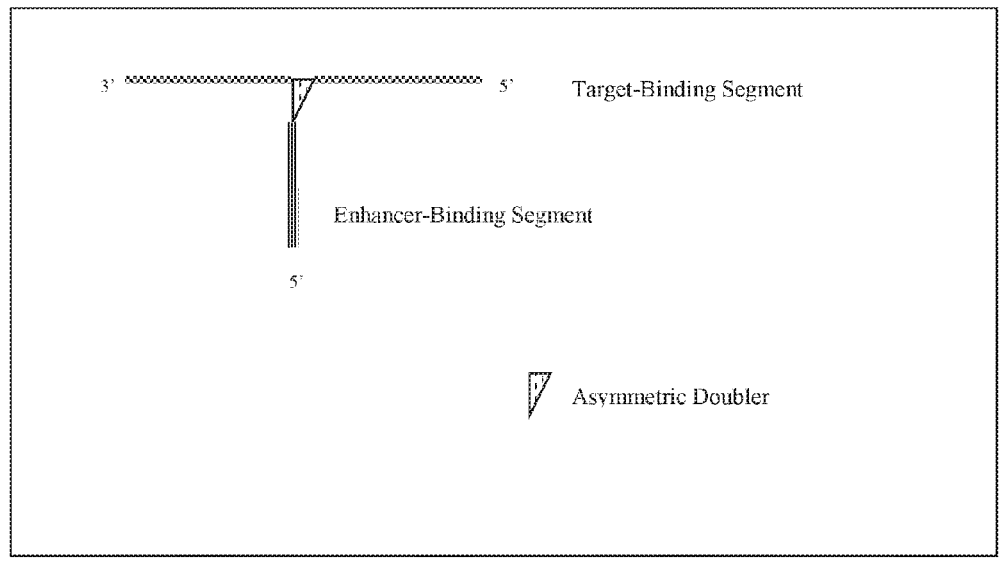
FIG. 3 illustrates schematically the structure of a T-linker.
Figure 4:
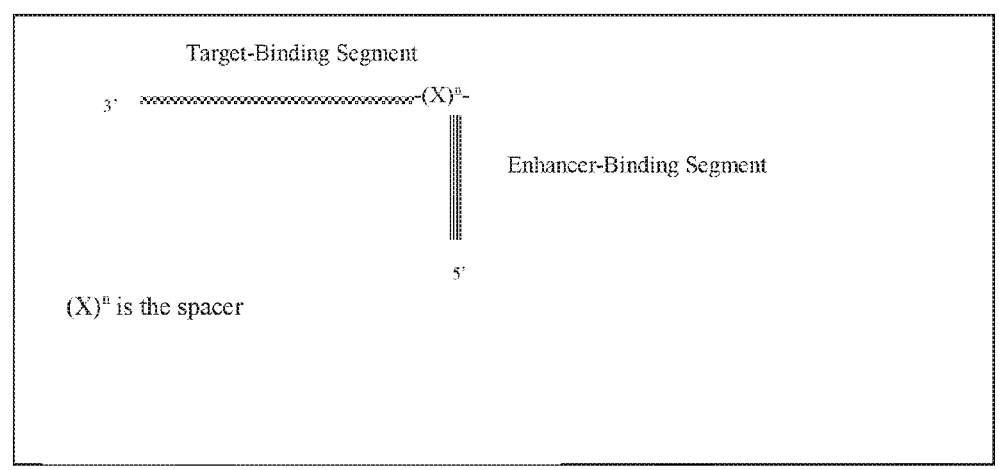
FIG. 4 illustrates schematically the structure of a L-linker.

In some embodiments, the linker comprises two segments. The first segment is a target-binding segment containing a nucleic acid sequence that is complementary to a segment of the target sequence of interest. The second segment is a nucleic acid sequence that is complementary to one segment of an enhancement probe, and hence, it is herein referred to as an enhancer-binding segment. In some embodiments, the linker has a L-structure. In some embodiments the linker has a T-structure. The target-binding segment of the T-linker is a linear nucleic acid sequence separated by an asymmetric doubler phosporamidite, as shown in FIG. 3. The enhancer-binding segment is connected to one site of the doubler phosporamidite. L-linker is a linear nucleic acid sequence including a number of nonspecific nucleotides, which form a spacer to separate the target-binding segment from the enhancer-binding segment, as shown in FIG. 4. With either linker structure, upon hybridization of the target-binding segment of the linker to the linker-binding segment of a target sequence, the enhancer-binding segment remains as a free port for attachment of the enhancement probes.

T-linker can be synthesized according to the method disclosed by M. S. Shchepinov using an asymmetric doubler phosporamidite, *Glen Research*, Vol. 12, No. 1, Nov. 1999, which is herein incorporated by reference in its entirety. The doubler phosphoramidite has two primary hydroxyl groups protected with DMT (4,4'-dimethoxytrityl) and Fmoc (N-alpha-(9-fluorenyl-methyloxycarbonyl)). Once the doubler phosporamidite is incorporated into the target-binding segment sequence, the remaining target-binding segment sequence is built upon the DMT-protected arm. After the synthesis of the target-binding segment is completed, the Fmoc arm is deprotected and an enhancer-binding segment sequence can be synthesized. In other words, T-linker can be synthesized in two steps. The first step incorporates a doubler phorporamidite into the target-binding segment sequence and the second step adds on the enhancer-binding sequence at the doubler phosphoramidite site. This results in a branched oligonucleotides with two 5' ends. The method of synthesizing T-linkers has been described in U.S. Pat. No. 7,482,122, which is incorporated by reference in its entirety.

Several T-linkers have been synthesized with the doubler phosphoramidite incorporated into different positions of the target-binding segment sequence. More specifically, one has the doubler phosphoramidite in the middle of a 20 base target-binding segment sequence; one has the doubler phosphoramidite positioned after 15 bases of a 20 base target-binding segment; and one has the doubler phosphoramidite positioned after 20 bases of a 23 base target-binding segment, as shown in Table 1.

TABLE 1

Example T- and L- Linker Sequences

| Probe | Length | Sequence (5'-3') |
|---|---|---|
| L- Primary Probe 1 | 41 | AGCCGGCTAGGCCGACGGATT"GAGATCTCCTCGACACCGCC" (SEQ ID NO: 22) |
| L- Primary Probe 2 | 51 | AGCCGGCTAGGCCGACGGATT"CCTCGACACCGCCCTTAGAGTCTCCGGAAC" (SEQ ID NO: 23) |
| L- Primary Probe 3 | 41 | AGCCGGCTAGGCCGACGGATT"GCCCTTAGAGTCTCCGGAAC" (SEQ ID NO: 24) |

| Probe | Branch Point | Target-binding segment sequence (5'-3') | Enhancer linker segment Sequence (5'-3') |
|---|---|---|---|
| T- Primary Probe 1 | 10/10 | "GAGATCTCCT" (SEQ ID NO: 15) X"CGACACCGCC" (SEQ ID NO: 16) | AGCCGGCTAGGCCGAC (SEQ ID NO: 17) |
| T- Primary Probe 2 | 15/5 | "GAGATCTCCTCGACA" (SEQ ID NO: 18) X"CCGCC" (SEQ ID NO: 19) | AGCCGGCTAGGCCGAC (SEQ ID NO: 17) |
| T- Primary Probe 3 | 20/3 | "GAGATCTCCTCGACACCGCC" (SEQID NO: 20) X-"TCT" (SEQ ID NO: 21) | AGCCGGCTAGGCCGAC (SEQ ID NO: 17) |

Note:
Target-binding segment sequence is in quote " "

Various L-linker have also been synthesized, as shown in Table 1. These linear oligonucleotides comprise a target-binding segment sequence, an enhancer-binding segment sequence and a spacer which separate the target-binding segment sequence and the enhancer-binding segment sequence. The enhancer-binding segment in the L-linker is like a tail, freely suspending after the target-binding segment, because neither the enhancer-binding segment sequence, nor the spacer, hybridizes to the target sequence. The spacer in the L-linker can be a number of non-specific nucleotides, a spacer phosphoramidite, or other suitable spacers known in the art. The syntheses of these linkers were completed using a standard protocol for linear oligonucleotide synthesis on the ABI DNA Synthesizer. Furthermore, because of the linear nature of this linker, cartridge purification was performed to obtain full length sequence.

Figure 5:
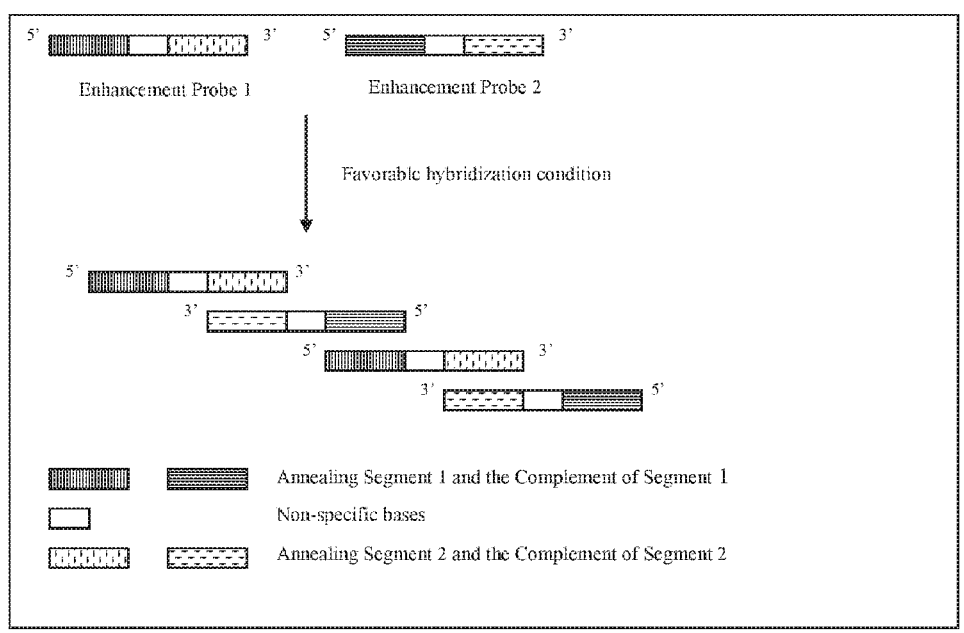
FIG. 5 illustrates the hybridization pattern of the first and second enhancement probe sequence.

The first and second enhancement probes are a pair of linear single strand nucleic acid sequences, and each has a first binding moiety at its first terminus (indicated by element "a" in FIG. 1) and a second binding moiety at its second terminus (indicated by element "b" in FIG. 1). As illustrated in FIG. 5, the sequence of each enhancement probe comprises a first annealing segment, a second annealing segment, and a spacer between the two segments. The first annealing segment of the first enhancement probe within the pair is complementary to the enhancer-binding segment sequence of the linker, which hybridizes to the enhancer-binding segment under a hybridization condition. Within the pair the first annealing segment of the second enhancement probe is complementary to the second annealing segment of the first enhancement probe, and the second annealing segment of the second enhancement probe is complementary to the first annealing segment of the first enhancement probe. Under a hybridization condition, the first and the second enhancement probes anneal with each other to form a staggered chain which links a plurality of enhancement probes to the linker.

In some embodiments, the sequence of the enhancer-binding segment of the linker is the same as the sequence of the second annealing segment of the second enhancement probe. In the enhancement probe sequence, the spacer does not bind to the target sequence, the linker or the enhancement probes. Suitable examples of the spacers include a number of non-specific nucleotides, a spacer phosphoramidite, or other suitable spacers known in the art.

As illustrated in FIGS. 1 and 2, each of the first and second enhancement probes has a first binding moiety (a) at the first terminus thereof, and a second binding moiety (b) at the second terminus thereof. The first binding moiety (a) at the first terminus has a chemical binding property specific to the capturer chemical functional group (A) distributed on the surface of the dual-functional capture particles, which under an appropriate chemical reaction condition binds to the capturer chemical functional group of the dual-functional capture particles. The binding may be direct between the first binding moiety (a) at the first terminus of the enhancement probes and the capturer chemical functional group of the dual-functional capture particles, or through an intermediate agent. The intermediate agent reacts with both the first binding moiety (a) at the first terminus of the enhancement probes and the capturer chemical functional group of the dual-functional capture particles to conjugate the two entities.

For the purpose of the present invention, the first binding moiety (a) of the enhancement probes and the capturer chemical functional group (A) of the dual-functional capture particles do not bind with each other during the hybridization process of the enhancement probes described above. Instead, the two chemical entities bind with each other under a specific chemical reaction condition that is introduced after hybridization of the enhancement probes and removal of unbound enhancement probes, as further described hereinafter. The binding reaction may be triggered by a specific chemical reaction condition, for example, addition of a catalyst, activation by light, activation by a specific pH or temperature, or a condition that triggers a redox reaction. Preferably, the chemical reaction is fast, with limited incubation requirement.

Various known chemical functional groups can be used for the first binding moiety (a) at the first terminus of the enhancement probes, which bind specifically to the capturer chemical functional group of the dual-functional capture particles. For example, as described above in reference to the dual-functional capture particles, the first binding moiety (a) of the first and second enhancement probes can be an azide functional group, which binds with a propargyl functional group on the dual-functional capture particles in a cycloaddition reaction catalyzed by Cu(I). Alternatively, the first binding moiety (a) of the first and second enhancement probes can be a propargyl functional group, which binds with an azide functional group on the dual-functional capture particles in the same cycloaddition reaction.

The second binding moiety (b) at the second terminus of the enhancement probes has a chemical binding property specific to the binding functional group on the reporter, which under an appropriate chemical reaction condition binds to the binding functional group on the reporter. The chemical reaction condition for the second binding moiety (b) at the second terminus of the enhancement probes and the binding functional group on the reporter may be unique for these two chemical function groups, or may be the same as the reaction condition for the binding reaction between the first binding moiety (a) at the first terminus of the enhancement probe and the capturer chemical functional group of the dual-functional capture particles described above. In the latter situation, the binding reactions at both the first and second termini of the enhancement probes may be initiated at the same time. Various known chemical functional groups can be used for the second binding moiety (b) at the second terminus of the enhancement probes, which bind specifically to the binding functional group on the reporter.

In an exemplary embodiment as illustrated in FIG. 5, the sequence of both enhancement probe 1 and enhancement probe 2 comprise three sections (5' to 3'): (1) annealing segment 1 or the complement of segment 1; (2) non-specific nucleotides, or bases; and (3) annealing segment 2 or the complement of segment 2. The non-specific bases are short strings of random bases inserted to separate the two annealing segments. However, these non-specific bases within enhancement probe 1 are not complementary to the non-specific bases of enhancement probe 2. These bases remain single stranded after the annealing of the two enhancement probes because of the staggered pattern formed.

The sequence length of the enhancement probe can be varied depending on the application to be used. Prior to synthesis of a pair enhancement probes, each enhancement probe sequence was put through NCBI (National Center for Biotechnology Information) BLASTN 2.2.6 to check if there were any significant matches in the database. This prevents potential non-specific binding of an enhancement probe to a nucleic acid region (viral, bacterial, human) other than their designated complementary sequences designed into the instant enhance signal amplification method.

Table 2 shows a number of pairs of enhancement probe sequences synthesized. Each sequence was synthesized using standard procedures on an oligonucleotide synthesizer (ABI DNA Synthesizer, Forest City, Calif.).

TABLE 2

Example Enhancement Probe Sequences

| Enhancement Probe (EP) | Annealing Segment 1 (5'-3') | Non-specific bases (5'-3') | Annealing Segment 2 (5'-3') |
|---|---|---|---|
| EP 1 (57 bases) | ACTTGCGTCGGCCTAGCC GGCT (SEQ ID NO: 1) | ATATATTA (SEQ ID NO: 2) | TCAGGCGACGGCTGAATCGGA AAGGCC (SEQ ID NO: 3) |
| EP 2 (57 bases) | AGCCGGCTAGGCCGACG CAAGT (SEQ ID NO: 4) | TCCCTACG (SEQ ID NO: 5) | GGCCTTTCCGATTCAGCCGTCG CCTGA (SEQ ID NO: 6) |
| EP 1A (45 bases) | TGCGTCGGCCTAGCCGGC T (SEQ ID NO: 7) | AT | TCAGGCGACGGCTGAATCGGA AAG (SEQ ID NO: 8) |
| EP 1B (45 bases) | AGCCGGCTAGGCCGACG CA (SEQ ID NO: 9) | TC | CTTTCCGATTCAGCCGTCGCTG A (SEQ ID NO: 10) |
| EP 1C (33 bases) | GTCGGCCTAGCCGGCT (SEQ ID NO: 11) | AT | TCAGGCGACGGCTGA (SEQ ID NO: 12) |
| EP1D (33 bases) | AGCCGGCTAGGCCGAC (SEQ ID NO: 13) | TC | TCAGCCGTCGCCTGA (SEQ ID NO: 14) |

After the first and second enhancement probe sequence is synthesized as described above, the first and second binding moieties are linked to the first and second terminus, respectively, via appropriate chemical reactions. Various known chemical reactions for conjugation of a chemical functional group to an oligonucleotide can be used for connection of the first and second binding moieties to the termini of each enhancement probe sequence.

Hybridization of the target sequence with the dual-functional capture particles and the first enhancement probe with the linker, and hybridization between the first and second enhancement probes can be carried out under known hybridization conditions. Table 3 illustrates three example hybridization conditions. The hybridization can be carried out in a suitable reaction vessel. The term "reaction vessel" used herein refers to a device which can be used to perform the hybridization reactions and the washing steps, which includes, but is not limited to, test tube, container, column, and filter.

TABLE 3

Hybridization Conditions

| Condition | Hybridization between linker and first enhancement probe | Hybridization between the first and second enhancement probes |
|---|---|---|
| 1 | 10X annealing buffer 60° C., at least 45 minutes | lithium succinate buffer* 60° C., at least 45 minutes |
| 2 | 1.8-2.0M guanidinium thiocyanate room temperature, at least 10 minutes | Lithium succinate buffer 60° C., at least 45 minutes |
| 3 | 1.8-2.0M guanidinium thiocyanate, room temperature, at least 10 minutes | 1.8-2.0M guanidinium thiocyanate room temperature, at least10 minutes |

*0.1M lithium succinate buffer: 125 mM lithium hydroxide, 95 mM succinic acid, 1.5 mM EDTA, 1.5 mM EGTA, 8.5% lithium lauryl sulfate.

In some embodiments, the reporter comprises a particle with a signal generating molecule and a binding functional group (indicated by element "B" in FIG. 2) immobilized thereon. The particle may be a suitable polymer particle, for example polystyrene particle or other polymer particles, with a diameter from about 1 to about 10 micrometer (μm). Various methods of conjugating chemical functional groups to polymer particles can be used for connecting the signal generating molecule and the binding functional group to the particle of the reporter. The binding functional group (B) of the reporter has a chemical binding property specific to the second binding moiety (b) at the second terminus of the first and second enhancement probes, which under an appropriate chemical reaction condition binds to the second binding moiety of the enhancement probes.

Various known chemical functional groups can be used for the binding functional group (B) of the reporter, which bind specifically to the second binding moiety (b) of the first and second enhancement probes. In one exemplary embodiment, the binding functional group (B) of the reporter is a thiol functional group, and the second binding moiety (b) of the enhancement probes is an amine functional group. A reaction to couple thiol functional group with an amine functional group by a sulfo-SMCC cross-linking reagent (4-(N-Maleimidomethyl)cyclohexane-1-carboxylic acid 3-sulfo-N-hydroxysuccinimide ester sodium salt) can be used for binding of the binding functional group (B) of the reporter with the second binding moiety (b) of the enhancement probes. Alternatively, the binding functional group (B) of the reporter is an amine functional group, and the second binding moiety (b) of the enhancement probes is a thiol functional group. The same chemical reaction and cross-linking reagent can be used for binding of the reporter with the enhancement probes.

The particle of the reporter has a size smaller than a pore size of a filter for removing the unbound reporter in the measurement method. On the other hand, the dual-functional capture particle has a size larger than the pore size of the filter, and therefore, in the process of separating unbounded reporter, the dual-functional capture particles are retained by the filter. In an exemplary embodiment, the dual-functional capture particle has a diameter of about 70 μm, and the particle of the reporter has a diameter about 6 μm. In such an embodiment, a polypropylene column is used. The column is cylindrical with a polyethylene filter of 40-50 μm pores at the bottom of the column. Moreover, in some embodiments the signal generating molecule and the binding functional group of the reporter may be one molecular assembly, which generates a detectable signal in one hand and binds to the second binding moiety of the enhancement probes on the other hand. In such embodiments, the particle may not be needed for the reporter.

Various known chemicals can be used as the signal generating molecule of the reporter. In some embodiments, the signal generating molecule is a chemiluminescent or fluorescent molecule, and the signal measurement can be carried out using chemiluminescence or fluorescence detectors. When the signal generating molecule is a chemiluminescent molecule, the method further comprises adding a chemiluminescent triggering solution prior to measuring the signal.

In an exemplary embodiment, acridinium $C_2$ NHS ester (4-(2-succinimidyl-oxycarbonylethyl) phenyl-10-acridinium-9-carboxylate trifluoromethyl sulfonate), from Assay Designs (Ann Arbour, Mich.), was used as the signal generating molecule of the reporter. Acridinium $C_2$ NHS ester can be triggered by a hydrogen peroxide solution. Acridinium ester reacts instantaneously (about 1 to 5 seconds) with hydrogen peroxide under alkaline condition to produce a light signal at 430 nm. The signal can be measured by a luminometer.

The mechanism of the detection method is described hereinafter in reference to FIGS. 1 and 2. As shown in FIG. 1, when a single strand nucleic acid target sequence of interest is exposed to dual-functional capture particles under a hybridization condition, the target sequence hybridizes with the capture sequence on the dual-functional capture particles, which forms a target-capture complex. After removing unbound target sequence, a linker is added to the target-capture complex under a hybridization condition. The target-binding segment of the linker hybridizes with the linker-binding segment of the target sequence. After removing unhybridized or unbound linker, the first and second enhancement probes are added under a hybridization condition. The first and second enhancement probes anneal with each other and form a staggered chain extending from the linker, which forms a capture-target-linker-enhancement probe complex, as shown in FIG. 1.

After removing unhybridized or unbound first and second enhancement probes, the capture-target-linker-enhancement probe complex is subjected to a condition under which a chemical binding reaction between the first binding moiety (a) of the first and second enhancement probes and the capturer chemical functional group (A) on the dual-functional capture particles is triggered. This results in binding of the first terminus of the first and second enhancement probes to the dual-functional capture particles, while leaving second terminus of the enhancement probes free standing. As described above, the binding can be either direct between the enhancement probes and the dual-functional capture particles, or through an intermediate agent which is involved in the binding reaction.

At this step, the capture-target-linker-enhancement probe complex can be denatured first to release the enhancement probes before triggering the binding reaction between the enhancement probes and the dual-functional capture particles. Alternatively, the capture-target-linker-enhancement probe complex is directly subjected to a condition that triggers the binding reaction between the first binding moiety (a) of the enhancement probes and the capturer chemical functional group (A) on the dual-functional capture particles. The formation of covalent bonds or ionic bonds between the first binding moiety of the enhancement probes and the capturer chemical functional group on the dual-functional capture particles interrupts the hydrogen bonds between enhancement probes in the staggered chain, which results in release of the enhancement probes.

In the above described exemplary embodiment, the capturer chemical functional group (A) of the dual-functional capture particles is a propargyl functional group, and the first binding moiety (a) of the first and second enhancement probes is an azide functional group, or vice versa. At this step, copper sulfate is added to trigger the Cu-catalyzed azide-alkyne cycloaddition reaction. This reaction is carried out at room temperature, which results in binding of the first terminus of the first and second enhancement probes to the dual-functional capture particles.

Then, the reporter is added. The binding functional group (B) of the reporter reacts with the second binding moiety (b) at the second terminus of the first and second enhancement probes, which results in binding of the reporter to the enhancement probes that are bound to the dual-functional capture particles, as illustrated in FIG. 2. In the above described exemplary embodiment, the binding functional group (B) of the reporter is a thiol functional group, and the second binding moiety (b) of the enhancement probes is an amine functional group, or vice versa. At this step, a sulfo-SMCC cross-linking reagent is added for the binding reaction between the binding functional group (B) of the reporter and the second binding moiety (b) of the enhancement probes. The binding reaction is carried out at room temperature.

The unbound reporter can be removed by proper means. In an example, unbound reporter is removed by filtering through a filter (indicated by the grid in broken lines in FIG. 2) that has a pore size larger than the size of the particle of the reporter, but smaller than the size of the dual-functional capture particles. After removing unbound reporter, the signal generated by the signal generating molecule on the bounded reporter can then be detected. The presence of the target sequence, or quantitation of the target sequence in a sample can be determined according to the signal detected.

In the above description the reporter is added after binding of the enhancement probes to the dual-functional capture particles. Alternatively, the reporter can be added first, wherein the reporter binds to the second binding moiety at the second terminus of the first and second enhancement probes in the staggered chain. The binding of a large number of particles of the reporter to the enhancement probes destabilizes the structure of the capture-target-linker-enhancement probe complex which is solely based on hydrogen bonds. Subsequently, the binding reaction between the enhancement probes and the dual-functional capture particles may be triggered. Furthermore, in some embodiments the reporter may be added at the same time of triggering the binding reaction between the enhancement probes and the dual-functional capture particles.

As illustrated in FIGS. 1 and 2, in the capture-target-linker-enhancement probe complex, a plurality of enhancement probes are linked to one target sequence through the linker. After releasing the enhancement probes from said complex and binding them to the dual-functional capture particles as described above, the detected signal directly correlates to the amount of the enhancement probes bound to the dual-functional capture particles. Therefore, the detected signal for one target sequence is substantially amplified through the enhancement probes. Moreover, as described above, covalent bond forms between capturer chemical functional group (A) of the dual-functional capture particles and the first binding moiety (a) of the first and second enhancement probes, as well as between the enhancement probes and the report, which is more advantageous than hydrogen bonding through hybridization. The strong bonding between the capture particles and the enhancement probes improves detection sensitivity and reduces background noise.

In some further embodiments, the method of the present invention comprises a further stage of signal enhancement. In such embodiments, the reporter described above is used as an intermedium binding agent rather than a signal generating entity, which is referred to herein as an intermedium coupler. Same as the reporter described above, the intermedium coupler comprises a binding functional group (B) which has the same binding property specific to the second binding moiety (b) at the second terminus of the first and second enhancement probes. On the other hand, instead of a signal generating molecule in the reporter, the intermedium coupler comprises a coupler sequence which is a single strand nucleic acid sequence complementary to a segment of a third enhancement probe. The third enhancement probe has another segment that is complementary to a segment of a fourth enhancement probe. The complementary nucleic acid sequence relationship between the third and fourth enhancement probes is in the same manner as that described above between the first and second enhancement probes. Therefore, under a favorable hybridization condition the third and fourth enhancement probes hybridize with each other and form a staggered chain. Instead of the first and second binding moieties at the two termini of the first and the second enhancement probes, each of the third and fourth enhancement probes comprises a signal generating molecule at one terminus. Therefore, the staggered chain formed by hybridized third and fourth enhancement probes carries numerous signal generating molecules. The signal generating molecules can be the same as those in the reporter described above.

In some embodiments, the intermedium coupler comprises a particle with binding functional group (B) and the coupler sequence immobilized thereon. Similar to the reporter, the particle may be a suitable polymer particle, for example polystyrene particle or other polymer particles, with a diameter from about 1 to about 10 micrometer (µm). The unbound intermedium coupler in the above described process can be removed by filtering with an appropriate filter.

In the embodiments using the intermedium coupler, instead of adding the reporter after binding of the first and second enhancement probes with the dual-functional capture particles, the intermedium coupler is added. The binding functional group (B) of the intermedium coupler binds with the second binding moiety (b) of the first and second enhancement probes same as that described above in reference to the reporter. Then, the third and fourth enhancement probes are added under a hybridization condition. The third enhancement probe anneal with the coupler sequence, and the third and fourth enhancement probes anneal with each other to form a staggered chain extending from the coupler sequence. After removal of unbound third and fourth enhancement probes, the signal from the signal generating molecules on the hybridized third and fourth enhancement probes in the staggered chain is measured.

In such a further enhancement process, each first or second enhancement probe bound to the dual-functional capture particles is further linked to numerous third and fourth enhancement probes, each of which carries a signal generating molecule. Therefore, the signal associated with one target sequence is further amplified.

As can be appreciated, the method of the present invention enhances the detectable signal in the measurement of a target sequence, which improves detection sensitivity of an assay without the expensive and time consuming PCR process.

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of detecting nucleic acids with an enhanced signal, comprising:

exposing a single strand nucleic acid target sequence of interest to dual-functional capture particles, each dual-functional capture particle comprising a capture sequence complementary to a segment of the target sequence and a capturer chemical functional group, both the capture sequence and the capturer chemical functional group being immobilized on and distributed throughout a surface of the dual-functional capture particles;

hybridizing the target sequence with the capture sequence on the dual-functional capture particles to form a target-capture complex;

removing unbound target sequence;

adding a linker comprising a target-binding segment complementary to a linker-binding segment of the target sequence and an enhancer-binding segment, and hybridizing the linker with the target sequence;

removing unbound linker;

adding a first enhancement probe and a second enhancement probe, the first enhancement probe comprising a first annealing segment complementary to the enhancer-binding segment of the linker, a second annealing segment, a first binding moiety at a first terminus of the first enhancement probe, and a second binding moiety at a second terminus of the first enhancement probe; the second enhancement probe comprising a first annealing segment complementary to the second annealing segment of the first enhancement probe, a second annealing segment complementary to the first annealing segment of the first enhancement probe, a first binding moiety at a first terminus of the second enhancement probe, and a second binding moiety at a second terminus of the second enhancement probe; and hybridizing the first enhancement probe with the linker, and the second enhancement probe with the first enhancement probe, wherein multiple of the first and second enhancement probes anneal with each other to form a staggered chain extending from the linker, thereby forming a capture-target-linker-enhancement probe complex;

removing unbound first and second enhancement probes;
triggering a chemical binding reaction between the first binding moiety at the first terminus of the first and second enhancement probes and the capturer chemical functional group on the dual-functional capture particles, thereby binding the first and second enhancement probes to the dual-functional capture particles;
adding a reporter comprising a signal generating molecule and a binding functional group specific to the second binding moiety at the second terminus of the first and second enhancement probes, thereby binding the reporter to the first and second enhancement probes through the binding functional group;
removing unbound reporter;
detecting a signal from the signal generating molecule on bounded reporter; and
determining the presence of the target sequence according to the signal.

2. The method of claim 1 further comprising exposing the capture-target-linker-enhancement probe complex to a denaturing condition prior to said triggering chemical binding reaction between the first binding moiety at the first terminus of the first and second enhancement probes and the capturer chemical functional group on the dual-functional capture particles.

3. The method of claim 1, wherein the signal generating molecule is a chemiluminescence or a fluorescence molecule.

4. The method of claim 3 further comprising triggering the signal generating molecule using a triggering solution prior to detecting the signal.

5. The method of claim 1, wherein the reporter comprises a particle with the signal generating molecule and the binding functional group immobilized thereon.

6. A method of detecting nucleic acids with an enhanced signal, comprising:
exposing a single strand nucleic acid target sequence of interest to dual-functional capture particles, each dual-functional capture particle comprising a capture sequence complementary to a segment of the target sequence and a capturer chemical functional group, both the capture sequence and the capturer chemical functional group being immobilized on and distributed throughout a surface of the dual-functional capture particles;
hybridizing the target sequence with the capture sequence on the dual-functional capture particles to form a target-capture complex;
removing unbound target sequence;
adding a linker comprising a target-binding segment complementary to a linker-binding segment of the target sequence and an enhancer-binding segment, and hybridizing the linker with the target sequence;
removing unbound linker;
adding a first enhancement probe and a second enhancement probe, the first enhancement probe comprising a first annealing segment complementary to the enhancer-binding segment of the linker, a second annealing segment, a first binding moiety at a first terminus of the first enhancement probe, and a second binding moiety at a second terminus of the first enhancement probe; the second enhancement probe comprising a first annealing segment complementary to the second annealing segment of the first enhancement probe, a second annealing segment complementary to the first annealing segment of the first enhancement probe, a first binding moiety at a first terminus of the second enhancement probe, and a second binding moiety at a second terminus of the second enhancement probe; and hybridizing the first enhancement probe with the linker, and the second enhancement probe with the first enhancement probe, wherein multiple of the first and second enhancement probes anneal with each other to form a staggered chain extending from the linker, thereby forming a capture-target-linker-enhancement probe complex;
removing unbound first and second enhancement probes;
triggering a chemical binding reaction between the first binding moiety at the first terminus of the first and second enhancement probes and the capturer chemical functional group on the dual-functional capture particles, thereby binding the first and second enhancement probes to the dual-functional capture particles;
adding an intermedium coupler comprising a coupler sequence and a binding functional group specific to the second binding moiety at the second terminus of the first and second enhancement probes, and binding the intermedium coupler with the first and second enhancement probes through the binding functional group;
adding a third enhancement probe and a fourth enhancement probe, the third enhancement probe comprising a first annealing segment complementary to the coupler sequence of the intermedium coupler, a second annealing segment, and a signal generating molecule at one terminus of the third enhancement probe; the fourth enhancement probe comprising a first annealing segment complementary to the second annealing segment of the third enhancement probe, a second annealing segment complementary to the first annealing segment of the third enhancement probe, and a signal generating molecule at one terminus of the fourth enhancement probe; and hybridizing the third enhancement probe with the intermedium coupler, and the fourth enhancement probe with the third enhancement probe, wherein multiple of the third and fourth enhancement probes anneal with each other to form a staggered chain extending from the intermedium coupler;
removing unbound third and fourth enhancement probes;
detecting a signal from the signal generating molecule on bounded third and fourth enhancement probes; and
determining the presence of the target sequence according to the signal.

7. The method of claim 6 further comprising exposing the capture-target-linker-enhancement probe complex to a denaturing condition prior to said triggering chemical binding reaction between the first binding moiety at the first terminus of the first and second enhancement probes and the capturer chemical functional group on the dual-functional capture particles.

8. The method of claim 6, wherein the signal generating molecule is a chemiluminescence or a fluorescence molecule.

9. The method of claim 8 further comprising triggering the signal generating molecule using a triggering solution prior to detecting the signal.

10. The method of claim 6, wherein the intermedium coupler comprises a particle with the coupler sequence and the binding functional group immobilized thereon.

* * * * *

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: Probe

<400> SEQUENCE: 1
acttgcgtcg gcctagccgg ct                                          22

<210> SEQ ID NO 2
<211> LENGTH: 8
<212> TYPE: DNA
<213> ORGANISM: Artificial Sequence
<220> FEATURE:
<223> OTHER INFORMATION: Probe

<400> SEQUENCE: 2 atatatta                                                           8

<210> SEQ ID NO 3
<211> LENGTH: 27
<212> TYPE: DNA
<213> ORGANISM: Artificial Sequence
<220> FEATURE:
<223> OTHER INFORMATION: Probe

<400> SEQUENCE: 3
tcaggcgacg gctgaatcgg aaaggcc                                     27

<210> SEQ ID NO 4
<211> LENGTH: 22
<212> TYPE: DNA
<213> ORGANISM: Artificial Sequence
<220> FEATURE:
<223> OTHER INFORMATION: Probe

<400> SEQUENCE: 4
agccggctag gccgacgcaa gt                                          22

<210> SEQ ID NO 5
<211> LENGTH: 8
<212> TYPE: DNA
<213> ORGANISM: Artificial Sequence
<220> FEATURE:
<223> OTHER INFORMATION: Probe

<400> SEQUENCE: 5 tccctacg                                                           8

<210> SEQ ID NO 6
<211> LENGTH: 27
<212> TYPE: DNA
<213> ORGANISM: Artificial Sequence
<220> FEATURE:
<223> OTHER INFORMATION: Probe

<400> SEQUENCE: 6
ggcctttccg attcagccgt cgcctga                                     27

<210> SEQ ID NO 7
<211> LENGTH: 19
<212> TYPE: DNA
<213> ORGANISM: Artificial Sequence

```
<220> FEATURE:
<223> OTHER INFORMATION: Probe

<400> SEQUENCE: 7
tgcgtcggcc tagccggct                                                  19

<210> SEQ ID NO 8
<211> LENGTH: 24
<212> TYPE: DNA
<213> ORGANISM: Artificial Sequence
<220> FEATURE:
<223> OTHER INFORMATION: Probe

<400> SEQUENCE: 8
tcaggcgacg gctgaatcgg aaag                                            24

<210> SEQ ID NO 9
<211> LENGTH: 19
<212> TYPE: DNA
<213> ORGANISM: Artificial Sequence
<220> FEATURE:
<223> OTHER INFORMATION: Probe

<400> SEQUENCE: 9
agccggctag gccgacgca                                                  19

<210> SEQ ID NO 10
<211> LENGTH: 23
<212> TYPE: DNA
<213> ORGANISM: Artificial Sequence
<220> FEATURE:
<223> OTHER INFORMATION: Probe

<400> SEQUENCE: 10
ctttccgatt cagccgtcgc tga                                             23

<210> SEQ ID NO 11
<211> LENGTH: 16
<212> TYPE: DNA
<213> ORGANISM: Artificial Sequence
<220> FEATURE:
<223> OTHER INFORMATION: Probe

<400> SEQUENCE: 11
gtcggcctag ccggct                                                     16

<210> SEQ ID NO 12
<211> LENGTH: 15
<212> TYPE: DNA
<213> ORGANISM: Artificial Sequence
<220> FEATURE:
<223> OTHER INFORMATION: Probe

<400> SEQUENCE: 12
tcaggcgacg gctga                                                      15

<210> SEQ ID NO 13
<211> LENGTH: 16
<212> TYPE: DNA
<213> ORGANISM: Artificial Sequence
<220> FEATURE:
<223> OTHER INFORMATION: Probe

<400> SEQUENCE: 13
agccggctag gccgac                                                     16
```

```
<210> SEQ ID NO 14
<211> LENGTH: 15
<212> TYPE: DNA
<213> ORGANISM: Artificial Sequence
<220> FEATURE:
<223> OTHER INFORMATION: Probe

<400> SEQUENCE: 14
tcagccgtcg cctga                                                    15

<210> SEQ ID NO 15
<211> LENGTH: 10
<212> TYPE: DNA
<213> ORGANISM: Artificial Sequence
<220> FEATURE:
<223> OTHER INFORMATION: Probe

<400> SEQUENCE: 15
gagatctcct                                                          10

<210> SEQ ID NO 16
<211> LENGTH: 10
<212> TYPE: DNA
<213> ORGANISM: Artificial Sequence
<220> FEATURE:
<223> OTHER INFORMATION: Probe

<400> SEQUENCE: 16
cgacaccgcc                                                          10

<210> SEQ ID NO 17
<211> LENGTH: 16
<212> TYPE: DNA
<213> ORGANISM: Artificial Sequence
<220> FEATURE:
<223> OTHER INFORMATION: Probe

<400> SEQUENCE: 17
agccggctag gccgac                                                   16

<210> SEQ ID NO 18
<211> LENGTH: 15
<212> TYPE: DNA
<213> ORGANISM: Artificial Sequence
<220> FEATURE:
<223> OTHER INFORMATION: Probe

<400> SEQUENCE: 18
gagatctcct cgaca                                                    15

<210> SEQ ID NO 19
<211> LENGTH: 5
<212> TYPE: DNA
<213> ORGANISM: Artificial Sequence
<220> FEATURE:
<223> OTHER INFORMATION: Probe

<400> SEQUENCE: 19 ccgcc                                                                5

<210> SEQ ID NO 20
<211> LENGTH: 20
<212> TYPE: DNA
<213> ORGANISM: Artificial Sequence
<220> FEATURE:
<223> OTHER INFORMATION: Probe
```

<400> SEQUENCE: 20
gagatctcct cgacaccgcc                                               20

<210> SEQ ID NO 21
<211> LENGTH: 3
<212> TYPE: DNA
<213> ORGANISM: Artificial Sequence
<220> FEATURE:
<223> OTHER INFORMATION: Probe

<400> SEQUENCE: 21 tct                                                                 3

<210> SEQ ID NO 22
<211> LENGTH: 41
<212> TYPE: DNA
<213> ORGANISM: Artificial Sequence
<220> FEATURE:
<223> OTHER INFORMATION: Probe

<400> SEQUENCE: 22
agccggctag gccgacggat tgagatctcc tcgacaccgc c                       41

<210> SEQ ID NO 23
<211> LENGTH: 51
<212> TYPE: DNA
<213> ORGANISM: Artificial Sequence
<220> FEATURE:
<223> OTHER INFORMATION: Probe

<400> SEQUENCE: 23
agccggctag gccgacggat tcctcgacac cgcccttaga gtctccggaa c            51

<210> SEQ ID NO 24
<211> LENGTH: 41
<212> TYPE: DNA
<213> ORGANISM: Artificial Sequence
<220> FEATURE:
<223> OTHER INFORMATION: Probe

<400> SEQUENCE: 24
agccggctag gccgacggat tgcccttaga gtctccggaa c                       41